United States Patent [19]

Duvernay et al.

[11] 4,304,875

[45] Dec. 8, 1981

[54] POLYURETHANE FOAMING COMPOSITION COMPRISING TRIORGANOSILYLATED POLYPENTAERYTHRITOL STABILIZER

[75] Inventors: Maurice Duvernay, Saint-Genis-Laval; Francesco Farina; André Guillaume, both of Lyons, all of France

[73] Assignee: Rhone-Poulenc Industries, Paris, France

[21] Appl. No.: 195,884

[22] Filed: Oct. 10, 1980

[30] Foreign Application Priority Data

Oct. 11, 1979 [FR] France ................. 79 25309

[51] Int. Cl.³ .................... C08G 18/14; C08G 18/00; C07F 7/02
[52] U.S. Cl. .................................. 521/112; 521/129; 521/125; 521/126; 521/127; 521/131; 521/904; 556/446
[58] Field of Search .................. 521/112; 556/446

[56] References Cited

U.S. PATENT DOCUMENTS

| | | | |
|---|---|---|---|
| 2,288,754 | 7/1942 | Story | 44/78 |
| 3,206,415 | 9/1965 | Koepnick et al. | 521/112 |
| 3,381,019 | 4/1968 | Morehouse | 521/112 |
| 3,935,133 | 1/1976 | van Leeuwen | 521/170 |
| 4,016,163 | 4/1977 | Kanner et al. | 521/111 |
| 4,067,828 | 1/1978 | Kanner et al. | 521/111 |

FOREIGN PATENT DOCUMENTS 2288754 6/1976 France .
2291995 6/1976 France .

OTHER PUBLICATIONS

Suchanec-Anal. Chem. 37, No. 11, Oct. 1965, pp. 1361-1365.
Published European Patent Application 761, Feb. 1979.

*Primary Examiner*—H. S. Cockeram
*Attorney, Agent, or Firm*—Burns, Doane, Swecker & Mathis

[57] ABSTRACT

A flexible, elastic, uniform polyurethane foam is cold foamed and set from a composition of matter comprising (i) a polyisocyanate, (ii) a polyether-polyol having a molecular weight ranging from 800 to 50,000 and at least 2.1 hydroxyl radicals per mol, of which hydroxyl radicals at least 35% are primary hydroxyl radicals, (iii) a stabilizing amount of an organosilicon stabilizer therefor, and (iv) a blowing agent; said organo silicon stabilizer being a triorganosilylated polypentaerythritol having the structural formula:

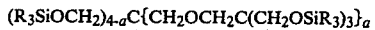

wherein each R, which may be the same or different, is methyl, ethyl or vinyl, at least one R per each —SiR₃ group being methyl, and further wherein a is 1, 2, 3 or 4.

20 Claims, No Drawings

POLYURETHANE FOAMING COMPOSITION COMPRISING TRIORGANOSILYLATED POLYPENTAERYTHRITOL STABILIZER

BACKGROUND OF THE INVENTION

1. Field of the Invention

The present invention relates to the preparation of "cold-cast" flexible polyurethane foams by expansion in molds, the foaming compositions containing very small amounts of organosilicon stabilizers selected from among the triorganosilylated polypentaerythritols. The resultant foams have good physical properties, in particular high elasticity.

2. Description of the Prior Art

The so-called "cold-cast" flexible polyurethane foams, i.e., foams which do not require subsequent heating, after removal from the mold, to complete the cross-linking or curing thereof, have been manufactured and used for several years. To prepare such foams, it is essential to employ, in addition to modified or unmodified polyisocyanates, foaming agents, catalysts and stabilizers, polyether-polyols which contain at least 10%, numerically, of primary hydroxyl radicals.

These polyether-polyols are used together with organosilicon compound stabilizers having a structure markedly different from that of the polysiloxane-polyoxyalkylene block copolymers which are used for the preparation of foams requiring a heat after-treatment.

Thus, these organosilicon compounds can be triorganosilylated polyols prepared by the reaction of low molecular weight polyols, such as trimethylolpropane or pentaerythritol, with triorganohalogenosilanes such as trimethylchlorosilane or dimethylvinylchlorosilane (French Patent No. 2,288,754); such triorganosilylated polyols are used in amounts of 0.05% to 3% by weight relative to the polyether-polyols.

Other organosilicon compounds, having a slightly different structure, are also employed in amounts on the same order (compare U.S. Pat. Nos. 2,935,133, 4,016,163 and 4,067,828, French Patent No. 2,291,995 and Published European Patent Application No. 761).

Although these amounts are rather low, the manufacturers of foams have constantly strived to reduce them even further because of the relatively high price of the organosilicon compounds vis-a-vis the other constituents of the foams.

SUMMARY OF THE INVENTION

Accordingly, a major object of the present invention is the provision of an improved foaming composition comprising a greatly reduced amount of a particular organosilicon stabilizer, which composition is readily converted into an improved polyurethane foam.

Briefly, the present invention features the preparation of the so-called "cold-cast" flexible polyurethane foams in which foaming compositions, obtained by mixing, principally, polyether-polyols having a molecular weight of between 800 and 50,000 and containing at least 2.1 hydroxyl radicals per mol (of which radicals, at least 35% are primary hydroxyl radicals), polyisocyanates, water, catalysts and organosilicon stabilizers, are poured into molds, exposed to the atmosphere, and after the foam has had time to foam and set it is removed from the mold, the process being characterized in that the stabilizers, utilized in amounts ranging from 0.001 to 1% by weight relative to the polyether-polyols, are triorganosilylated polypentaerythritols having the structural formula:

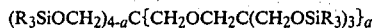

in which the symbols R, which are identical or different, represent methyl, ethyl or vinyl radicals, at least one radical R per each —$SiR_3$ group being a methyl radical, and the symbol a represents 1, 2, 3 or 4.

DETAILED DESCRIPTION OF THE INVENTION

More particularly, the aforenoted triorganosilylated polypentaerythritols are per se known; same are described, for example, in the article by Richard R. Suchanec, *Analytical Chemistry*, Volume 37, No. 11, pages 1361–1365 (October, 1965). Furthermore, same are readily prepared by reaction of silanes and/or of silazanes, respectively of the formulae $R_3SiX$ and $R_3SiNH—SiR_3$ (wherein the symbol X represents a halogen atom, preferably chlorine, and the symbols R are as defined above), with polypentaerythritols. This reaction is akin to that presented in French Patent No. 2,288,754, in which triorganosilylated polyols are prepared from the same silylating agents having the formulae $R_3SiX$ and $R_3SiNH-SiR_3$ and from polyols related to the polypentaerythritols, and comprising pentaerythritol, 1,1,1-trimethylolethane and 1,1,1-trimethylolpropane.

The recommendations and variations of the disclosed method of operation in French Patent No. 2,288,754 are accordingly applicable to the preparation of the subject triorganosilylated polypentaerythritols; in particular:

(i) It is preferable, if the silylating agent is the silane $R_3SiX$, to neutralize the halogen-containing acid HX which is formed, with ammonia or with a tertiary amine such as triethylamine or pyridine;

(ii) The use of an equimolar mixture of the silylating agents $R_3SiX$ and $R_3SiNHSiR_3$ obviates the need for the basic neutralizing agent because the halogen-containing acid HX is neutralized by the ammonia emanating from the disilazane $R_3SiNHSiR_3$, this process being illustrated, in the case of the preparation of hexatrimethylsilylated dipentaerythritol, by the following equation:

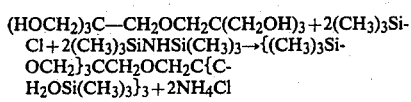

(iii) The reaction temperature is conveniently controlled by diluting the reaction mixture with organic solvents such as toluene or xylene, used in an amount equal to 10 to 50% by weight of the reactants.

The polypentaerythritol starting materials (namely, di-, tri-, tetra- and penta-pentaerythritol) are commercially available compounds which often contain a small percentage of the other polyols in addition to that desired.

By way of illustration, the following triorganosilylated polypentaerythritols are exemplary:

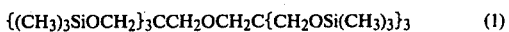 (1)

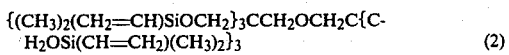 (2)

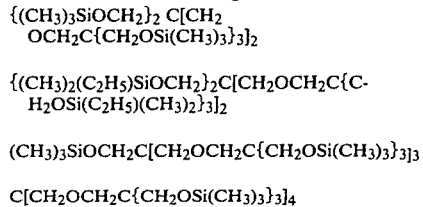

$$\{(CH_3)_2(C_2H_5)SiOCH_2\}_2C[CH_2OCH_2C\{CH_2OSi(C_2H_5)(CH_3)_2\}_3]_2 \quad (4)$$

$$(CH_3)_3SiOCH_2C[CH_2OCH_2C\{CH_2OSi(CH_3)_3\}_3]_3 \quad (5)$$

$$C[CH_2OCH_2C\{CH_2OSi(CH_3)_3\}_3]_4 \quad (6)$$

The subject triorganosilylated polypentaerythritols are advantageously incorporated into the foaming compositions in an amount ranging from 0.001 to 1% by weight, preferably 0.005 to 0.1%, relative to the weight of the polyether-polyols.

As above indicated, the foaming compositions are prepared by intimately admixing the polyether-polyols, polyisocyanates, water and/or other foaming agents, catalysts, stabilizers and, optionally, auxiliary adjuvants and additives such as crosslinking agents.

The polyether-polyols employed have molecular weights on the order of 750 to 50,000, preferably of 1,500 to 20,000; same contain, on the average, from 2.1 to 5 hydroxyl radicals per mol, of which radicals 35% to 90% are primary hydroxyl radicals. The hydroxyl number of these polyethers typically does not exceed 45.

The polyether-polyols are prepared by polymerization of epoxides such as ethylene oxide, propylene oxide, butylene oxide, tetrahydrofuran or styrene oxide, in the presence of initiators containing active hydrogen atoms, such as polyols, polyamines and alkanolamines.

The following initiators are noted as being exemplary: ethylene glycol, diethylene glycol, glycerol, hexa-1,2,6-triol, trimethylolethane, trimethylolpropane, sucrose, ethylenediamine, diethylenetriamine, ethanolamine and isopropanolamine.

The high content of primary hydroxyl radicals in the polyether-polyols is achieved both through the choice of the initiators (which have an average functionality of at least 2.1) and through blocking the polyalkylene chains with ethylene oxide.

The organic polyisocyanates employed are either aliphatic, cycloaliphatic, araliphatic, aromatic or heterocyclic in nature; typically, the following are employed: the toluylene diisocyanates (mixtures of the 2,4- and 2,6-isomers in the molar ratio of 80:20 or 65:35), ethylene diisocyanate, propylene diisocyanate, hexamethylene diisocyanate, 4,4'-diisocyanatodiphenylmethane, 1,5-diisocyanato-naphthalene, 1,3-diisocyanatocyclohexane, the polymeric polyisocyanates, such as the polymethylene-polyphenyl isocyanates described, for example, in U.S. Pat. No. 2,683,730 or British Pat. Nos. 848,671 and 874,430, and the modified polyisocyanates, bearing carbodiimide, urethane, isocyanurate, biuret, allophanate or acylated urea groups, respectively described in U.S. Pat. Nos. 3,152,162, 3,394,164, 3,001,973 and 3,124,605, British Pat. No. 994,890 and German Patent No. 1,230,778.

The amount of polyisocyanates used must be sufficient to provide at least from 0.8 to 1.5, preferably from 0.9 to 1.15, —NCO radicals per active hydrogen present in the foaming compositions, the active hydrogen being provided principally by the polyether-polyols and the water.

The blowing or foaming agents are selected from among water and/or organic substances which are volatile or decompose at a temperature above ambient temperature. Preferably, water and the volatile halogenated alkanes such as monofluorotrichloromethane, difluorodichloromethane and 1,1,2-trichloro-1,2,2-trifluoro-ethane are employed.

Water is usually employed in an amount of 1 to 6 parts by weight, and the volatile halogenated alkanes are usually employed in an amount of 2 to 20 parts by weight, per 100 parts by weight of polyether-polyols.

The catalysts are organic, preferably tertiary monoamines and polyamines, such as triethylamine, 1,4-diaza-2,2,2-bicyclo-octane (or triethylenediamine), N,N,N',N'-tetramethylethylenediamine, N-ethylmorpholine, N,N'-dimethylpiperazine, N,N-dimethylcyclohexylamine, bis-(1,3-dimethylamino)-butane and bis-(2-dimethylamino-ethyl) ether.

Organometallic catalysts based on salts and oxides of tin, such as stannous 2-ethylhexanoate, dibutyl-tin dilaurate and dibutyl-tin oxide, can also be included.

Crosslinking agents can be introduced into the formulation to improve the mechanical properties of the foams; these crosslinking agents possess active hydrogens. By way of illustration, the following are exemplary crosslinking agents:
  (i) Polyols, such as glycerol, butane-1,4-diol, butane-1,3-diol, trimethylolpropane, the triol having the formula $CH_3CH_2C(CH_2OCH_2CH_2OH)_3$ and the condensates (having a high hydroxyl number) of alkylene oxides with polyols;
  (ii) Polyamines, such as 3,3'-dichloro-4,4'-diaminodiphenylmethane, dimethylaminopropylamine and N,N'-bis-(2-aminopropyl)-piperazine; and
  (iii) Alkanolamines, such as monoethanolamine, diethanolamine and triethanolamine, monoisopropanolamine, diisopropanolamine and triisopropanolamine.

Other ingredients or additives, such as reaction retarders, cell structure regulators, pigments, flameproofing agents, plasticizers, fungicides and bactericides, can also be included.

The foaming compositions are prepared by simple mixing, in optional sequence, of the various ingredients noted above, the polyisocyanates preferably being added last. In order to obviate, in industrial manufacture of the foams, the need for handling of all these ingredients within a very short period of time and in a restricted area, it is advantageous to form stable and homogeneous premixes which contain at least 2 ingredients; for example, these premixes may consist of: all of the ingredients except for the polyisocyanates; only the polyether-polyols and the organosilicon stabilizers; the polyether-polyols, the organosilicon stabilizers, the water and/or the blowing agents; or the polyisocyanates and the organosilicon stabilizers.

As the reaction is highly exothermic, the polyurethane foams are produced without applying an external source of heat. The reaction can, however, be accelerated by preheating the molds in which the expansion of the foams takes place. The molds can be closed or opened; they are closed for the preparation of molded shaped articles which must possess a well-defined shape and surface appearance, while they are open for the production of bulky blocks or of blocks having a large surface.

The foams prepared according to the process of the present invention have a fine and uniform cell structure and a set of good physical properties, and, furthermore, shrink but little, if at all, after removal from the mold. They are especially useful for mattresses, furniture, wall coverings, packaging, and automotive accessories.

In order to further illustrate the present invention and the advantages thereof, the following specific examples are given, it being understood that same are intended only as illustrative and in nowise limitative.

EXAMPLE 1

Preparation of Hexatrimethylsilylated Dipentaerythritol 200 g of toluene, 254 g (1 mol, assuming 100% purity) of dipentaerythritol having the formula $(HOCH_2)_3C-CH_2OCH_2-C(CH_2OH)_3$ and 239 g (2.2 mols) of trimethylchlorosilane were introduced into a 2 liter reactor equipped with a thermometer sleeve, a stirrer, a dropping funnel and a condenser surmounted by an analyzer. The dipentaerythritol employed was a commercial product containing at least 38% by weight of hydroxyl groups and having a melting point of 212–217° C.

354 (2.2 mols) of hexamethyldisilazane were introduced into the dropping funnel.

The stirred contents of the flask were first heated to 50° C. At this temperature, the heating was discontinued and the hexamethyldisilazane was introduced into the flask at a rate sufficient to ensure that, because of the exothermicity of the silylation reaction, the temperature of the contents of the flask was within the range 55°–65° C.

The introduction of the hexamethyldisilazane was conducted over a period of about 2 hours; when same was completed, the contents of the flask were heated at reflux temperature for 1 hour and, after cooling to about 25° C., were treated first with 375 g of water and then with 200 g of water. This treatment removed the ammonium chloride formed.

The toluene solution which remained was gradually heated to about 100° C. under reduced pressure, namely, 2,500 Pa; such heating principally removed the toluene and the hexamethyldisiloxane, which originated from the hydrolysis of the excess of trimethylchlorosilane and of hexamethyldisilazane employed in the reaction.

175 g of toluene were then added to the residue remaining after such devolatilization, and the batch was again gradually heated to about 100° C. under a pressure of 2,500 Pa.

The residue obtained was filtered hot at about 60° C.

The filtrate (648 g) crystallized upon being permitted to remain at ambient temperature; the product melted at about 40°–42° C. and contained about 0.1% of hydroxyl groups (whereas pure dipentaerythritol contains 40% of hydroxyl groups).

Analysis by gas phase chromatography, combined with analysis by exclusion-diffusion chromatography on silica gel, indicated that the filtrate consisted substantially of:

(i) 92% of hexatrimethylsilylated dipentaerythritol having the formula $\{(CH_3)_3SiOCH_2\}_3C-CH_2-C\{CH_2OSi(CH_3)_3\}_3$;

(ii) 1.5% of tetratrimethylsilylated monopentaerythritol of the formula $\{(CH_3)_3SiOCH_2\}_4C$;

(iii) 4.5% of octatrimethylsilylated tripentaerythritol having the formula $\{(CH_3)_3SiOCH_2\}_2C[CH_2O-CH_2C-\{CH_2OSi(CH_3)_3\}_3]_2$; and (iv) 2% of unidentified products.

EXAMPLE 2

Preparation of Octatrimethylsilylated Tripentaerythritol

This preparation was similar to the procedure of Example 1 for the preparation of the hexatrimethylsilylated dipentaerythritol.

200 g of toluene, 186 g (0.5 mol, assuming 100% $(HOCH_2)_2C\{CH_2OCH_2C(CH_2OH)_3\}_2$ and 159 g (1.46 mols) of trimethylchlorosilane were introduced into the 2 liter reactor used in Example 1. The tripentaerythritol employed was a commercial product containing at least 35% of hydroxyl groups and having a melting point of 238°–240° C.

236 g (1.46 mols) of hexamethyldisilazane were introduced into the dropping funnel.

The contents of the flask were heated to about 60° C.; at this temperature, the hexamethyldisilazane was introduced into the flask at a rate sufficient to maintain the temperature of the contents of the flask at about 60°–65° C. The introduction of the hexamethyldisilazane required about 1 hour, 10 minutes.

The contents of the flask were then heated at reflux temperature for 1 hour; after cooling to about 25° C., the contents were treated first with 250 g of water and then with 150 g of water.

The toluene solution which remained was devolatilized by gradual heating to about 100° C., under a pressure of 2,500 Pa. 150 g of toluene were added to the residue from the devolatilization operation and the batch was again heated to about 100° C. under reduced pressure, namely, 2,500 Pa.

The residue obtained was filtered hot at about 50° C.

The filtrate (385 g) remained liquid upon being permitted to remain at ambient temperature, its viscosity being on the order of 580 mPa.s at 25° C.; same contained about 0.07% of residual hydroxyl groups (pure tripentaerythritol contains 36% of hydroxyl groups). Analysis by gas phase chromatography, together with analysis by exclusion-diffusion chromatography on silica gel, indicated that this filtrate consisted of:

(i) 88% of octatrimethylsilylated tripentaerythritol having the formula $\{(CH_3)_3SiOCH_2\}_2C[CH_2OCH_2C\{CH_2OSi(CH_3)_3\}_3]_2$;

(ii) 1.5% of hexatrimethylsilylated dipentaerythritol having the formula $\{(CH_3)_3SiOCH_2\}_3C-CH_2-C\{CH_2OSi(CH_3)_3\}_3$;

(iii) 7% of decatrimethylsilylated tetrapentaerythritol having the formula $(CH_3)_3SiOCH_2C[CH_2OCH_2-C\{CH_2OSi(CH_3)_3\}_3]_3$;

(iv) 0.5% of dodecatrimethylsilylated pentapentaerythritol having the formula $C[CH_2OCH_2-C\{CH_2OSi(CH_3)_3\}_3]_4$; and (v) 3% of unidentified products.

EXAMPLE 3

The following ingredients were successively introduced into a 2 liter reactor, equipped with a stirrer, and after the stirrer had been started:

(i) 1,000 g of a polyether-triol of molecular weight 5,000, containing about 75%, numerically, of primary hydroxyl groups, and having a hydroxyl number of 35;

(ii) 30 g of water;

(iii) 100 g of trichlorofluoromethane;

(iv) 2.7 g of 1,4-diaza-2,2,2-bicyclooctane; and (v) 4 g of an amino-ether having the formula }(CH₃)₂NCH₂CH₂}₂O.

After completion of the addition of the amino-ether, stirring of the mixture of ingredients was continued for 2 minutes.

147.8 g of the stable and homogeneous mixture obtained above (containing 130 g of polyether-triol) were introduced into a 300 cm³ reactor equipped with a variable-speed stirrer. 0.020 g of the hexatrimethylsilylated dipentaerythritol (melting at about 40°–42° C. and containing 0.1% of hydroxyl groups), and prepared in Example 1, was first added to the contents of the reactor, the hexatrimethylsilylated dipentaerythritol being diluted, to 10% strength, with octamethylcyclotetrasiloxane, such that 0.20 g of the diluted material was added; the batch was stirred for 15 seconds at 1,000 rpm.

58.1 g of a mixture consisting of 34.9 g of 4,4'-diisocyanato-diphenylmethane and 23.2 g of an 80:20 toluylene diisocyanate isomer mixture was then added; the batch was stirred for 6 seconds at 1,500 rmp. This sequence of operations resulted in the formation of a foaming composition; the latter was immediately poured into an aluminum mold having the dimensions 200×200×100 mm which had been heated to about 40° C.; and the mold was then closed. The mold was opened after a period of 10 minutes and the block of polyurethane foam contained therein was removed and cut into two substantially equal pieces having the dimensions 200×100×100 mm. Upon visual examination of the cut area of each piece it was found that the cells of the foam were fine and uniform; furthermore, there were no coarse cells in the form of "honeycombs" at the base of the block of foam.

One of the two pieces of the block of foam was maintained as is, and the other piece was manually calendered.

The volume of each piece of the block was measured after having been maintained for 5 hours at ambient temperature after release from the mold, and the shrinkage (expressed in % by volume) of the non-calendered piece, compared to the calendered part, was calculated from these measurements.

Samples were then cut from the core of the calendered piece after the latter had been maintained at ambient temperature for a period of 24 hours following release from the mold. (Other blocks of foam were prepared in accordance with the procedure defined above, and from the same ingredients, so as to have sufficient samples available for determining the properties of the foam).

The dimensions of these samples were 50×50×25 mm and 100×100×50 mm.

The samples of size 50×50×25 mm were used for measuring the density and the porosity. The porosity represents the number of liters of air which, in 1 minute, pass through samples which are exposed at right angles, over their large cross-section (50×50 mm₂) to a stream of air under a pressure of $1.0012 \times 10^5$ Pa.

The samples of size 100×100×50 mm were used to measure the rebound according to Standard Specification ASTM D 1564 T. The value of the rebound, expressed in cm, is defined as the distance between the point of impact of a steel ball dropping onto the sample (the sample being inclined at 45° C. to the axis of drop of the ball), and the point at which it begins to fall after rebounding.

Additionally, a comparison foam was produced following the above procedure and employing the same ingredients, but without the introduction of 0.020 g of the hexatrimethylsilylated dipentaerythritol. It was found, from visual examination of the cut area of the two pieces of the block of comparison foam, that the cellular structure was less fine than that of the foam containing the hexatrimethylsilylated dipentaerythritol; furthermore, coarse cells in the form of "honeycombs" were plainly visible at the base of the block of this comparison foam.

The pieces containing coarse cells were industrially unusable. Accordingly, same have to be discarded, and this entails loss of material.

The density, the porosity and the rebound were also measured on the calendered part of this comparison foam (the material being selected from the core of the foam, so as not to use the part containing the coarse cells), and the shrinkage, in % by volume, relative to the calendered part, was evaluated for the non-calendered part. The results relating to the two types of foam are summarized in the table below:

TABLE I

|  | density in g/l | porosity in l/min | rebound in cm | shrinkage in % by volume |
|---|---|---|---|---|
| Foam containing hexatrimethyl-silylated dipentaerythritol | 33.1 | 145 | 49.5 | 11% |
| Comparison foam | 34.1 | 155 | 49 | 8% |

Little difference is found between the physical properties of the foam produced with the hexatrimethylsilylated dipentaerythritol and those of the comparison foam; hence, the presence of the hexatrimethylsilylated dipentaerythritol does not cause deterioration of the physical properties.

By way of comparison, foams were produced in accordance with the procedure employed above for the preparation of the foam containing hexatrimethylsilylated dipentaerythritol, but such additive was replaced by the tetratrimethylsilylated pentaerythritol of the formula {(CH₃)₃SiOCH₂}₄C, the use of which, for the preparation of polyurethane foams, is described in French Patent No. 2,288,754. This tetratrimethylsilylated derivative was introduced in sufficient amount to provide a foam having a fine and uniform structure, without coarse cells.

It was found that it was necessary to use 0.2 g of this derivative, in place of 0.02 g of the hexatrimethylsilylated dipentaerythritol, namely, 10 times as much.

EXAMPLE 4

The following ingredients were successively introduced into the reactor used in Example 3:

(i) 1,000 g of the polyether-triol of Example 3;
(ii) 30 g of water;
(iii) 2 g of 1,4-diaza-2,2,2-bicyclooctane;
(iv) 4 g of dimethylaminopropylamine;
(v) 70 g of a propylene oxide/sucrose condensate;
(vi) 15 g of glycerol; and
(vii) 14 g of diethanolamine.

After completion of the addition of the diethanolamine, the mixture of the various ingredients was stirred for 5 minutes.

170.2 g of the stable and homogeneous mixture obtained above (containing 150 g of polyether-triol) were introduced into a 350 cm³ equipped with a variable-speed stirrer. 0.015 g of the octatrimethylsilylated tripentaerythritol (of viscosity 580 mPa.s at 25° C. and containing 0.07% of hydroxyl groups) prepared in Example 2 was firstly added to the contents of this reactor, the octatrimethylsilylated tripentaerythritol added being diluted to 10% strength with tetramethyltetravinylcyclotetrasiloxane, such that 0.15 g of the diluted material was added; the batch was stirred for 15 seconds at 1,000 rpm. Thereafter, 78 g of a mixture consisting of 19.5 g of 4,4'-diisocyanatodiphenylmethane and 58.5 g of an 80:20 isomer mixture of toluylene diisocyanates were added; the batch was stirred for 6 seconds at 1,500 rpm.

This sequence of operations resulted in the formation of a foaming composition which was immediately poured into an open cylindrical mold made of polyethylene and having a capacity of 6 liters. This composition was allowed to foam freely to form a block of foam; the latter was released from the mold 10 minutes after the introduction of the composition, and was then cut into two substantially equal pieces.

The cut area of each piece evidenced a foam which had a fine and uniform cell structure and was free from coarse cells, in the form of "honeycombs", usually found at the base of the blocks. One of the two pieces was maintained as is, and the other was manually calendered.

The measurements of the physical properties of the foam were carried out in accordance with the procedure set forth in Example 3; these measurements established the shrinkage of the non-calendered piece compared to the calendered piece, as well as the density, porosity and rebound of the calendered piece.

A comparison foam was produced by following the procedure employed above for the preparation of the foam containing the octatrimethylsilylated tripentaerythritol, but in the absence of such additive.

It was found that in contrast to the foam containing the octatrimethylsilylated tripentaerythritol, the comparison foam had an irregular cell structure; furthermore, cells in the form of "honeycombs" were visible at the base of the blocks of this foam.

Measurements indentical to those mentioned previously were carried out on this comparison foam; the results relating to the two foams are summarized in the table below:

TABLE II

|  | density in g/l | porosity in l/min | rebound in cm | shrinkage in % by volume |
|---|---|---|---|---|
| Foam containing octatrimethylsilylated tripentaerythritol | 33 | 166 | 49 | 0% |
| Comparison foam | 34 | 172 | 49.5 | 0% |

These results reflect that the two foams have very similar physical properties, thus, the incorporation of the octatrimethylsilylated tripentaerythritol does not detract from the properties of the flexible polyurethane foams.

EXAMPLE 5

The following were successively introduced into the reactor used in Example 3:
(i) 1,000 g of a polyether-triol which had a molecular weigth of 5,500, contained about 65%, numerically, of primary hydroxyl groups, and had a hydroxyl number of 28;
(ii) 30 g of water;
(iii) 1 g of 1,4-diaza-2,2,2-bicyclooctane;
(iv) 4 g of triethylamine; and
(v) 6 g of N,N'-bis-(2-aminopropyl)-piperazine.

After completion of the addition of the N,N'-bis-(2-aminopropyl)-piperazine, the mixture of the various ingredients was stirred for 3 minutes.

135.3 g of the stable and homogeneous mixture obtained above (containing 130 g of polyether-triol) were introduced into a 300 cm³ reactor equipped with a variable-speed stirrer. 0.040 g of the hexatrimethylsilylated dipentaerythritol (melting at about 40°–42° C. and containing 0.1% of hydroxyl groups) prepared in Example 1 was firstly added to the contents of this reactor, the hexatrimethylsilylated dipentaerythritol added being diluted to 10% strength with octamethylcyclotetrasiloxane, such that 0.4 g of the diluted material was added; the batch was stirred for 15 seconds at 1,000 rpm. Thereafter, 53.3 g of an 80:20 isomer mixture of toluylene diisocyanates, modified by reaction with tripropylene glycol, were added; the batch was stirred for 5 seconds at 1,500 rpm.

This sequence of operations resulted in the formation of a foaming composition which was immediately poured into an aluminum mold having the dimensions 200×200×100 mm.

The mold was closed; it was then opened after a period of 10 minutes, and the block of polyurethane foam contained in the mold was removed and then cut into two equal pieces having the dimensions 200×100×100 mm.

The cut area of each piece evidenced a foam having a fine and uniform structure, devoid of coarse cells at the base of the block.

One of the two pieces was maintained as is and the other was manually calendered. The measurements of the physical properties of the foam (density, porosity, rebound and shrinkage) were carried out in accordance with the procedure described in Example 3.

A comparison foam was produced by following the procedure employed above for the preparation of the foam containing the hexatrimethylsilylated dipentaerythritol, but in the absence of this additive; here again, as in Examples 3 and 4, the comparison foam differed from the foam containing the trimethylsilylated polypentaerythritol additive in having a coarser, less uniform structure, which burst at the base of the blocks, to form cells in the form of "honeycombs".

The measurements of the physical properties were subsequently carried out on this comparison foam. The results relating to the two foams are summarized in the table below:

TABLE III

|  | density in g/l | porosity in l/min | rebound in cm | shrinkage in % by volume |
|---|---|---|---|---|
| Foam containing hexatrimethyl- silylated dipentaerythritol | 33 | 155 | 50 | 0 |
| Comparison foam | 35 | 163 | 48.5 | 0 |

These results indicated that the two foams have virtually identical physical properties; accordingly, the hexatrimethylsilylated dipentaerythritol did not adversely affect the foams even when same was introduced in an amount which was twice as high (0.04 g per 130 g of polyether-triol) as that used in Example 3 (0.02 g per 130 g of polyether-triol).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A composition of matter adapted to cold foam into a flexible polyurethane foam, comprising (i) a polyisocyanate, (ii) a polyether-polyol having a molecular weight ranging from 800 to 50,000 and at least 2.1 hydroxyl radicals per mol, of which hydroxyl radicals at least 35% are primary hydroxyl radicals, (iii) a stabilizing amount of an organosilicon stabilizer therefor, and (iv) a blowing agent; said organosilicon stabilizer being a triorganosilylated polypentaerythritol having the structural formula:

$$(R_3SiOCH_2)_{4-a}C\{CH_2OCH_2C(CH_2OSiR_3)_3\}_a$$

wherein each R, which may be the same or different, is methyl, ethyl or vinyl, at least one R per each—SiR$_3$ group being methyl, and further wherein a is 1, 2, 3 or 4.

2. The composition of matter as defined by claim 1, said triorganosilylated polypentaerythritol stabilizer (iii) being present in an amount ranging from 0.001 to 1% by weight, based upon the weight of the polyether-polyol (ii).

3. The composition of matter as defined by claim 2, said stabilizer (iii) being present in an amount ranging from 0.005 to 0.1% by weight, base upon the weight of the polyether-polyol (ii).

4. The composition of matter as defined by claim 2, the hydroxyl number of the polyether-polyol (ii) not exceeding 45.

5. The composition of matter as defined by claim 2, the amount of polyisocyanate (i) being such as to provide therein from 0.8 to 1.5—NCO radicals per active hydrogen atom.

6. The composition of matter as defined by claim 2, said blowing agent (iv) comprising water.

7. The composition of matter as defined by claim 2, said blowing agent (iv) comprising a haloalkane.

8. The composition of matter as defined by claim 6, the amount of water being 1 to 6 parts by weight, per 100 parts by weight of the polyether-polyol (ii).

9. The composition of matter as defined by claim 7, the amount of haloalkane being 2 to 20 parts by weight, per 100 parts by weight of the polyether-polyol (ii).

10. The composition of matter as defined by claim 2, further comprising a catalytically effective amount of a crosslinking catalyst.

11. The composition of matter as defined by claim 10, further comprising at least one additive selected from the group consisting of a reaction retarder, a cell structure regulator, a pigment, a flameproofing agent, a plasticizer, a fungicide and a bactericide.

12. The composition of matter as defined by claim 2, said stabilizer (iii) having the structural formula:

$$\{(CH_3)_3SiOCH_2\}_3CCH_2OCH_2C\{CH_2OSi(CH_3)_3\}_3.$$

13. The composition of matter as defined by claim 2, said stabilizer (iii) having the structural formula:

$$\{(CH_3)_2(CH_2\!=\!CH)SiOCH_2\}_3CCH_2OCH_2C\{CH_2OSi(CH\!=\!CH_2)(CH_3)_2\}_3.$$

14. The composition of matter as defined by claim 2, said stabilizer (iii) having the structural formula:

$$\{(CH_3)_3SiOCH_2\}_2C[CH_2OCH_2OSi(CH_3)_3\}_3]_2.$$

15. The composition of matter as defined by claim 2, said stabilizer (iii) having the structural formula:

$$\{(CH_3)_2(C_2H_5)SiOCH_2\}_2C[CH_2OCH_2C\{CH_2OSi(C_2H_5)(CH_3)_2\}_3]_2.$$

16. The composition of matter as defined by claim 2, said stabilizer (iii) having the structural formula:

$$(CH_3)_3SiOCH_2C[CH_2OCH_2C\{CH_2OSi(CH_3)_3\}_3]_3.$$

17. The composition of matter as defined by claim 2, said stabilizer (iii) having the structural formula:

$$C[CH_2OCH_2C\{CH_2OSi(CH_3)_3\}_3]_4.$$

18. A flexible, elastic, uniform polyurethane foam devoid of honeycomb, comprised of the foamed and set composition of matter as defined by any one of claims 1 to 17.

19. A method for the preparation of the flexible, elastic, uniform polyurethane foam as defined by claim 18, comprising intimately admixing the several ingredients of the composition, charging a mold cavity with such admixture, and thence permitting such admixture to ambient foam and set within said mold cavity.

20. A shaped article comprising the flexible, elastic, uniform polyurethane foam as defined by claim 18.

* * * * *